United States Patent [19]
Blumberg et al.

[11] Patent Number: 6,153,438
[45] Date of Patent: Nov. 28, 2000

[54] RETENTION FACTOR DATABASE

[75] Inventors: Leonid M. Blumberg, Hockessin, Del.; Bruce D. Quimby, Lincoln University, Pa.; Matthew S. Klee, Wilmington, Del.

[73] Assignee: Hewlett-Packard Company, Palo Alto, Calif.

[21] Appl. No.: 08/859,630

[22] Filed: May 20, 1997

Related U.S. Application Data

[63] Continuation-in-part of application No. 08/846,977, Apr. 30, 1997, Pat. No. 5,827,946.

[51] Int. Cl.$^7$ .................................................. G01N 30/02
[52] U.S. Cl. ...................... 436/161; 73/23.25; 73/23.27; 73/23.36; 95/82; 95/87
[58] Field of Search ................................ 436/161; 95/82, 95/87; 73/23.25, 23.27, 23.36

[56] References Cited

U.S. PATENT DOCUMENTS

| | | | |
|---|---|---|---|
| 4,994,096 | 2/1991 | Klein et al. . | |
| 5,405,432 | 4/1995 | Snyder et al. | ........................... 95/82 |
| 5,827,946 | 10/1998 | Klee et al. | ........................... 73/23.36 |

OTHER PUBLICATIONS

Willard et al., Instrumental Methods of Analysis, Sixth Edition, Wadsworth Publishing, Belmont CA (1981) p. 435, 1981.
Chemical Abstracts, CA 127:265217, Svetlova et al., J. Anal. Chem. (Transl. of Zh. Anal. Khim.) (1997), 52(9), 868–870, 1997.
Chemical Abstracts, CA 103:177899, Abidi, J. Chromatogr. (1985), 324(2), 209–230, 1985.
"Standard Test Method For Detailed Analysis Of Petroleum Naphthas Through n–Nonane By Capillary Gas Chromatography"; ASTM Committee D–2 on Petroleum Products and Lubricants; Published Oct. 1992, Originally published as D 5134–90.
Hewlett–Packard Company Operation Manual, "5880A Gas Chromatograph PNA Analyzer, Operation 850", Oct. 1982, Revised Jul. 1983; Part No. 18900–90850.
Hewlett–Packard Company Operation Manual, "The HP5880A Gas Chromatograph and The HP85 Computer Configured for PNA Analysis"; 18900–90603; Mar. 1985 Rev. B, Apr. 1986 Rev C.

*Primary Examiner*—Jan Ludlow

[57] ABSTRACT

A method for identifying analytes of interest by referencing to a retention factor database corresponding to a plurality of identified analytes that is independent of column dimensions and carrier gas type while dependent upon stationary phase type ratio and a relative temperature program. The retention factor database is generated on a reference GC system in which the column head pressure is adjusted to ensure high reproducibility of retention times by locking the column void time and/or the retention time of an identified analyte to a specific value such that accurate retention factors (k) can be calculated in accordance with the formula:

$$k = \frac{(RT - VT)}{VT}$$

where VT is the void time of the column having a specified stationary phase and phase coating installed in a GC system operating in accordance to a specified temperature program (where time is expressed in units of column void time).

7 Claims, 5 Drawing Sheets

RETENTION TIME ADJUSTMENT
USING RT versus P CALIBRATION $$\text{PRESSURE ADJUSTMENT} = \frac{(RT_a - RT_{target})}{\frac{\Delta RT}{\Delta P}}$$

REQUIRED PRESSURE CHANGE = (ACTUAL RET. TIME − TARGET RET. TIME)$\frac{\Delta P}{\Delta T}$

RETENTION FACTOR DATABASE

CROSS-REFERENCE TO RELATED APPLICATIONS

This application is a Continuation-In-Part application which claims the benefit of and priority to U.S. patent application Ser. No. 08/846,977, filed Apr. 30, 1997, now U.S. Pat. No. 5,827,946.

FIELD OF THE INVENTION

The present invention relates to methods for identification of unknown analytes of interest and, more particularly, to creating a retention factor database that can be accessed for identifying analytes of interest by matching retention factors even though many of the column and operating parameters on a reference GC system used to create the retention factor database are different from the column and operating parameters of a locking GC system used for separating the analytes of interest.

BACKGROUND OF THE INVENTION

Gas chromatography is based on the premise that the combination of analytes making up a sample injected into a column within a gas chromatograph separate as they transverse the column at different rates and subsequently elute from the column at different retention times. Both operational parameters (column head pressure, carrier gas type and oven temperature) and column parameters (length, inside diameter, stationary phase type and thickness) contribute to an analyte's retention time.

It is known how to generate a calibration table of retention times corresponding to identified compounds passing through a column having specified column parameters (that are typically accurate to within 5%) configured in a reference gas chromatograph having a set of specified operating parameters. The retention time table is usually employed for identifying unknowns through analysis on the same system as the calibration table was formed. Also it might be used to assist in the identification of analytes of interest passing through other GC systems configured with a column having the same specified column parameters configured in a GC having the same specified operating parameters. Unfortunately, even slight variations of less than 1% between the reference GC systems column and operating parameters used to form the calibration table, and those of another GC system may result in large variations in retention time. In particular, variations may be due to instrument calibration, atmospheric temperature and pressure changes, oven design, column length and column degradation. Additionally, the accuracy of a table of retention times is subject to both operating and column parameter drift over the many weeks typically required to generate a table (especially if the table is large). Even though it is difficult to replicate exact retention times set forth in a retention time database, such a database is useful in illustrating the relative relationship between retention times such that through trial and error or lengthy cross-correlation, it is possible to positively identify unknown analytes of interest.

A popular "relative retention" approach to using chromatographic databases utilizes retention indices or Kovats indices that circumvent problems in getting the same retention time from instrument-to-instrument, column-to-column. In general, all prior art chromatography calibration table protocols that have been successfully employed for identifying unknown analytes are based on either relative retention times (retention indexes) or retention times related to a specific GC system having specified column and operating parameters that do not change (for example, during column maintenance). Attempts to replicate the identical column and operating parameters on another GC system or after column maintenance, is virtually impossible.

It would be advantageous to develop a method for the identification of analytes of interest by a factor that is not specific to the GC system and/or the column and operating parameters employed for separating the analytes. It would be advantageous to have a method for comparing the separations of samples generated on a number of different GC systems. It would be advantageous to provide for a plurality of individual GC systems optimized for specific purposes (speed, specific analyte, type of detector, column availability etc.) while retaining the ability to reference a single database for analyte identification. It would be advantageous to provide for a generic database that can be easily ported to multiple configurations of instruments including; on-line, fieldable, laboratory, detectors that operate at atmospheric pressure, detectors that operate at a vacuum and those having high resolution.

SUMMARY OF THE INVENTION

The invention is a method for identifying analytes of interest by referencing a retention factor database corresponding to a plurality of identified analytes that is independent of column dimensions and carrier gas type while dependent upon stationary phase type and ratio and a relative temperature program. The retention factor database is generated on a reference GC system in which the column head pressure is adjusted to ensure high reproducibility of retention times by locking the column void time and/or the retention time of an identified analyte to a specific value. The void time of the column and the retention times of a series of known analytes (standards) making up the database are directly related to the reference GC system. The reference GC system is periodically recalibrated during the measurement of retention times to maintain a locked condition by adjusting the column head pressure to maintain a constant column void time and/or a constant retention time for the identified analyte.

A retention factor (k) is calculated and stored in the database for each of the injected analytes in accordance with the following formula:

$$k = \frac{(RT - VT)}{VT}$$

where VT is the void time of the column having a specified stationary phase and phase ratio and RT is the retention time of the analytes injected into the reference GC system at a specified temperature program (where time is expressed in units of column void time). The retention factor (k) provides for the identification of the same analytes passing through any of the plurality of locking GC systems, regardless of column dimensions, carrier gas type or values of inlet or outlet pressures as long as the conditions of temperature program and carrier gas flow are scaled proportionally to the ratio of the void times in the locking GC system and the reference GC system.

In an alternative embodiment, the column void time VT in the formula for the retention factor (k) is replaced by a nominal void time (hereinafter, NVT) corresponding to the retention time of a slightly retained analyte that has a retention time that approaches the column void time. NVT is ascertained for both the retention factor database, and the locking GC system by injecting and measuring the retention time of a slightly retained analyte. The temperature program conditions for the locking GC system are scaled in accordance with the NVT. There are times when void time is not ascertainable, or may not be measured accurately and the use of NVT is preferred.

In another alternative embodiment of the invention, a virtual void time (hereinafter "VVT") is estimated based on the column and operating parameters of the locking GC system. The VVT is employed for calculating a virtual temperature program for the locking GC system. The column head pressure of the locking GC system is adjusted to lock the locking GC system to the retention factor database by identifying a particular analyte of interest that is identified in the output of the locking GC system and is also identified in the retention factor database and graphing retention factor (calculated using the VVT) versus pressure for a number of different pressures (both above and below a nominal pressure). A correction to the column pressure correction is ascertained by comparing the retention factor (RF) for the identified analyte in the retention factor database and curve fitting this value to the retention factor versus pressure graph.

A retention factor database may be accessed by a variety of different locking GC systems employing different column dimensions, carrier gas types under different inlet and outlet pressures for the identification of analytes of interest based on the retention factor (c) alone. Each retention factor database is specific only for the type of stationary phase, the phase ratio, and the temperature program relative to void time. An appropriate carrier gas flow rate is determined by the chromatographer for the locking GC system that is based on the column parameters (column type, length, inside diameter, stationary phase etc.) of the selected column. The void time for the selected column and retention times for analytes of interest are measured such that retention factors (k) can be calculated and employed for identifying the analytes of interest by reference to the retention factor database.

Completely automated analyses may be obtained from the use of this invention, including the use of a centralized retention factor database corresponding to a chromatographic method of wide importance or application. Such a database could be accessible from Internet enabled distributed chromatographs operating under locked conditions that still provide for individual requirements for speed, resolution, carrier gas type, or column capacity.

The invention provides for advantages in any one of the following areas: easy access to up-to-date data that is easily expanded and updated; independent reference by a diverse array of users that now have the opportunity to compare data and leverage chromatographic method development, increased confidence in results, easier implementation of analyzers that provide for preliminary peak identification without the requirement for running standards. Furthermore, the invention provides for easier troubleshooting, easier implementation of knowledge-based optimization for trouble shooting and enhanced pattern recognition.

Other aspects and advantages of the present invention will become apparent from the following detailed description, taken in conjunction with the accompanying drawings, illustrating by way of example the principles of the invention.

DETAILED DESCRIPTION OF THE PREFERRED EMBODIMENTS

The invention is a method for identifying analytes of interest by referencing a retention factor database corresponding to a plurality of identified analytes that is independent of column dimensions and carrier gas type while dependent upon stationary phase type and ratio and a relative temperature program. The invention provides for the generation of a database that is easily accessed by multiple GC instrument configurations to identify analytes of interest. The invention may be practiced on a prior art HP 6890 Gas Chromatograph with Electronic Pressure Control manufactured by Hewlett-Packard Company. GC systems offered by other manufactures may be employed for practicing the invention if they have the ability to accurately adjust column head pressure to defined values. Software executing on a computer commonly associated with the GC system that provides for automatic control of most operating parameters as well as the collection, integration and display of chromatographic results is modified to provide for generating a retention factor database and/or locking a GC system to a retention factor database.

Figure 1:
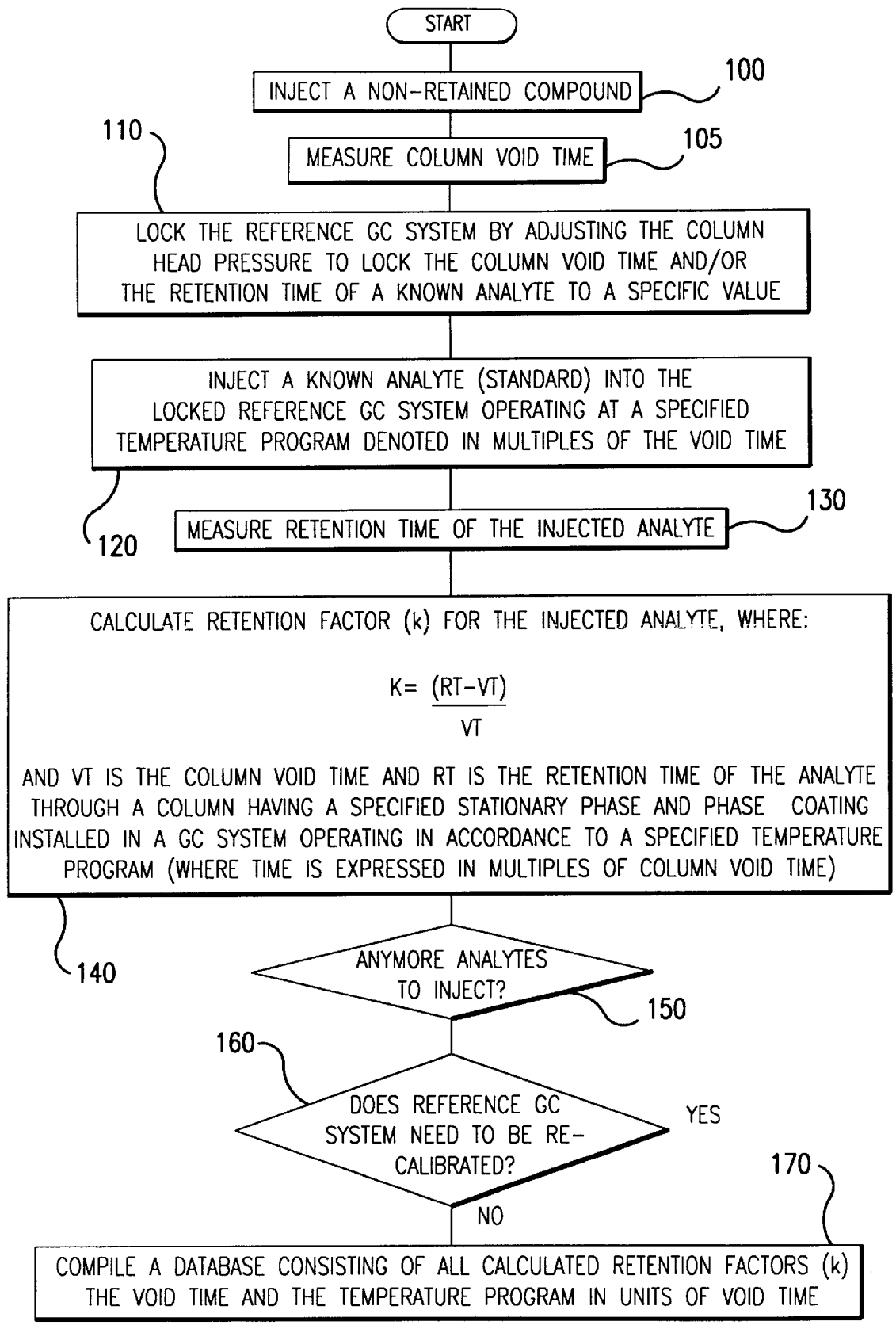
FIG. 1 is a flow chart illustrating the method steps for generating a retention factor database.
Figures 3A, 3B:
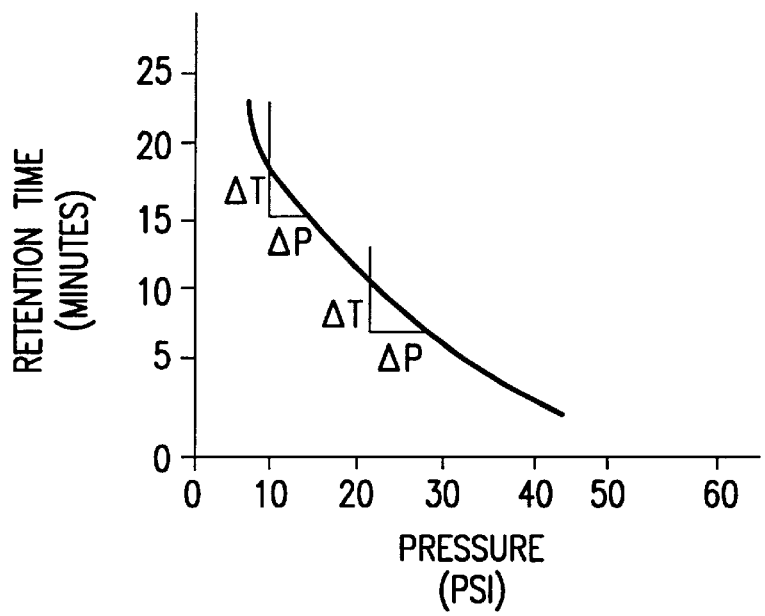
FIG. 3A shows a pressure adjustment formula.
FIG. 3B is a graph illustrating the retention time versus pressure relationships for accurately calculating the column head pressure required to lock the reference GC system as set forth in the flowchart of FIG. 1.

Software executing on a computer associated with a reference GC system is programmed in accordance with the flowchart as illustrated in FIG. 1 for generating a retention factor database under retention locked conditions. In particular, a non-retained compound is injected into a column installed in a reference GC system (step 100) and the column void time is measured (step 105). The reference GC system is locked by adjusting the column head pressure to a value calculated to lock the column void time and/or the retention time of a known analyte to a specific value (step 110). The process for calculating and adjusting the column head pressure to effect retention time locking is fully disclosed in commonly assigned U.S. patent application Ser. No. 08/728,868, filed on Oct. 10, 1996 (now abandoned) entitled "Automated Retention Time Locking" and hereby incorporated by reference. In particular, an adjustment to the column head pressure may be calculated in accordance to the formula set forth in FIG. 3A and/or by injecting a known analyte one or more times above a nominal pressure and one or more times below a nominal pressure, the results of which are graphed as illustrated in FIG. 3B such that a pressure adjustment required to lock the head pressure may be ascertained.

Once a locking pressure is ascertained, a series of known analytes (standards) are then injected into the locked reference GC system operating at a specified temperature program expressed in multiples of the void time (step 120) and the retention time of each injected analyte is measured. The reference GC system is operated in accordance with a temperature program where time is expressed in units of void time. A plurality of identified analytes ("standards") are injected serially into the reference GC system and the retention time for each analyte is measured. A retention factor (k) is calculated and stored in the database for each of the plurality of analytes of interest in accordance with the following formula:

$$k = \frac{(RT - VT)}{VT}$$

where VT is the column void time and RT is the retention time of the analyte through a column having a specified stationary phase and phase coating installed in a locking GC system operating in accordance to a specified temperature program (where time is expressed in multiples of column void time). In the preferred embodiment, periodic recalibrations are employed to ensure that the reference GC system remains locked to the initial calibration (as evidenced by the column void time or the retention time of a specified analyte), during the generation of all the retention factors making up the database.

Once generated, the retention factor database may be employed for the identification of a plurality of unknown analytes making up a sample injected into a GC system having the same stationary phase and ratio of that employed with the reference GC system and having possibly different column dimensions, different carrier gas type, and under different inlet and outlet pressures. For example, a chromatographer may wish to increase the speed of chromatography by using a shorter column and/or an increased column head pressure. Either of these factors will reduce the column void time and the retention times of retained analytes. However, by translating the temperature program into units of void time, it is possible to replicate the chromatography employed when generating the database such that analytes of interest may be identified by calculating the retention factor (k) based on the retention time of an analyte and the void time of the new column and looking up the identity of the analyte in the database. For example, if the void time of a column under a specified set of operating parameters is 30 seconds, then a 1 minute time plateau in a temperature program would be specified as one lasting two void times. Similarly, a ramp rate of 20 degrees centigrade per minute would be specified as 10 degrees centigrade per void time.

Figure 2:
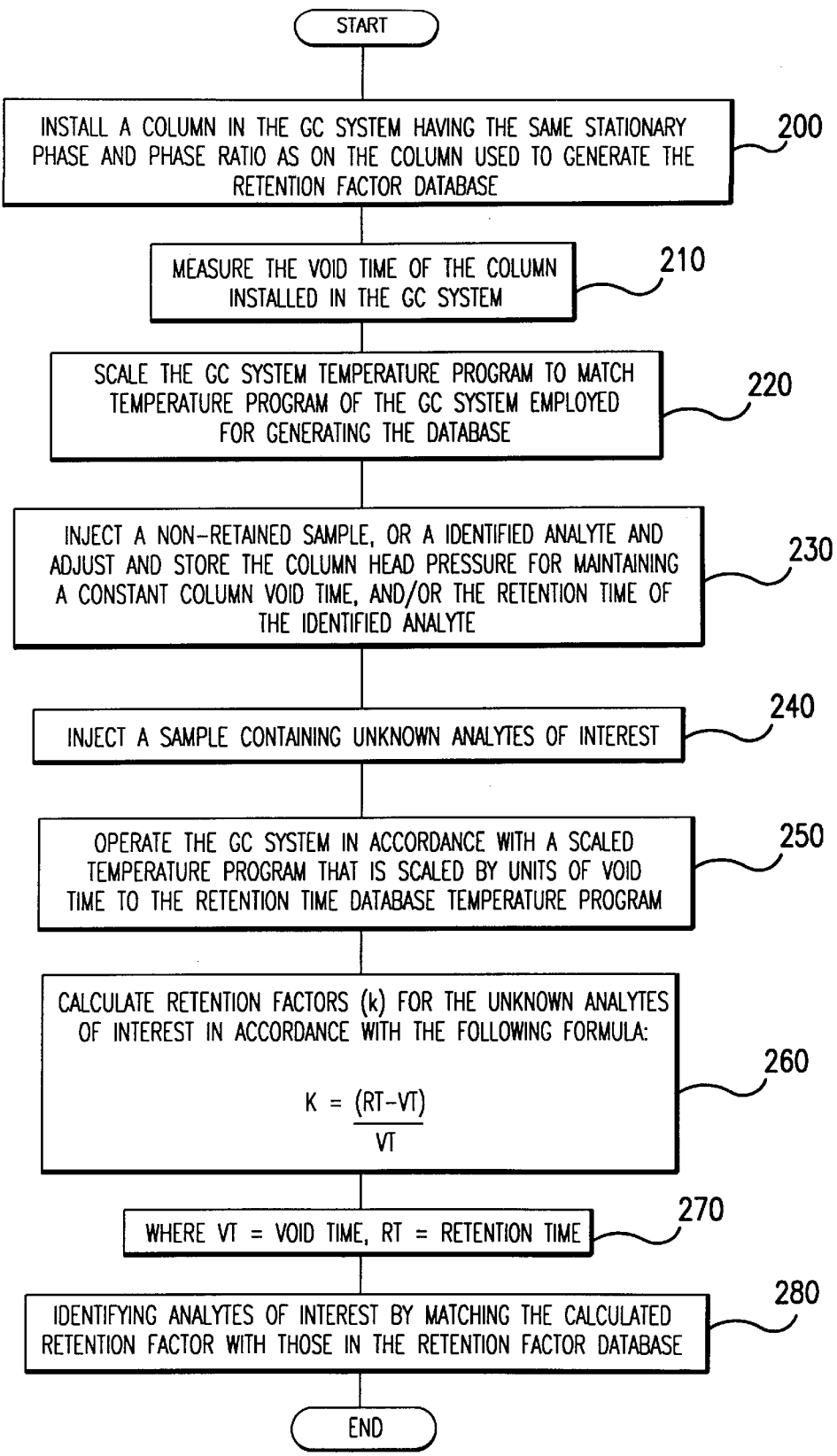
FIG. 2 is a flow chart illustrating the method steps for identifying analytes of interest by retention factor.

FIG. 2 illustrates method steps for identifying analytes of interest making up a sample injected into a column installed on a GC system, where the identification is based solely on matching retention factors stored in a retention factor database. The column installed in the GC system must have the same stationary phase and phase ratio as on the column used to generate the retention factor database (step 200). While slight variations in stationary phase ratio may still provide for the identification of analytes of interest, the accuracy of the retention time lock is limited. The void time of the column installed in the locking GC system is ascertained at a GC system temperature appropriate for the chromatographic method and column as determined by an experienced chromatographer (step 210). Once the void time of the column is ascertained (typically by injecting a non-retained compound such as nitrogen), the temperature program of the locking GC system is scaled in multiples of column void time to match the temperature program of the reference GC system employed for generating the database (step 220). A non-retained sample or an identified retained analyte is injected into the locking GC system and the column head pressure is adjusted to maintain a constant column void time and/or the retention time of the identified analyte, thereby locking all retention times (step 230). A sample containing unidentified analytes of interest is injected into the GC system (step 240). The locking GC system is operated in accordance with a scaled temperature program that is scaled by units of void time to the retention time database (step 250). The retention time for each unidentified analyte of interest eluting from the column is measured and employed for calculating a retention factor (k) in accordance with the following formula:

$$k = \frac{(RT - VT)}{VT}$$

where VT=void time, RT=retention time (step 260). All of the analytes of interest may be identified by matching the calculated retention factor with those in the retention factor database. However, the temperature program employed must be scaled to the temperature program associated with the retention factor data base in void time units.

In an alternative embodiment, the column void time VT in formula for the retention factor (k) is replaced by a nominal void time (hereinafter, NVT) corresponding to the retention time of a slightly retained analyte and has a retention time that approaches the column void time.

$$k = \frac{(RT - NVT)}{NVT}$$

where NVT is the retention time of a slightly retained analyte that approaches the void time of the column. NVT can be ascertained by injecting a slightly retained analyte into a locking GC system. The temperature program conditions must still be scaled appropriately and the same slightly retained analyte must be used each time NVT is calculated.

The invention provides a method for locking the retention times of a locking GC system by adjusting the locking GC system operational parameters to compensate for typical variations between the operational and column parameters of the locking GC system and those of the reference GC system which were used in the formation of the retention time database. Notwithstanding the ability to compensate for operational and column parameter variations, retention time locking requires precise oven temperature control, identical column parameters (dimensions, stationary phase chemistry and film thickness) and precise flow control. Oven temperature control is obtained by good oven design that provides for accurate control. Identical column parameters are obtained by proper column selection prior to installation within the locking GC system. In the preferred embodiment, precise flow control is provided by electronic pressure control as set forth in U.S. Pat. No. 4,994,096 issued on Feb. 19, 1991 to Klein et al and commonly assigned to Hewlett-Packard Company and which is hereby incorporated by reference. Other known techniques for precise flow control may also be employed.

A locking GC system may employ a retention factor database generated on a different GC system for identifying analytes as the retention factor automatically scales for different operating conditions by virtue of the void time. Once locked, a preliminary identification of analytes eluting from the column can be made by comparing (manually or automatically) the calculated retention factor to those in the retention factor database. While the preliminary identification may be sufficient for some applications, additional discrimination is required if a number of potential analytes of interest have relatively close retention factors.

Figure 4:
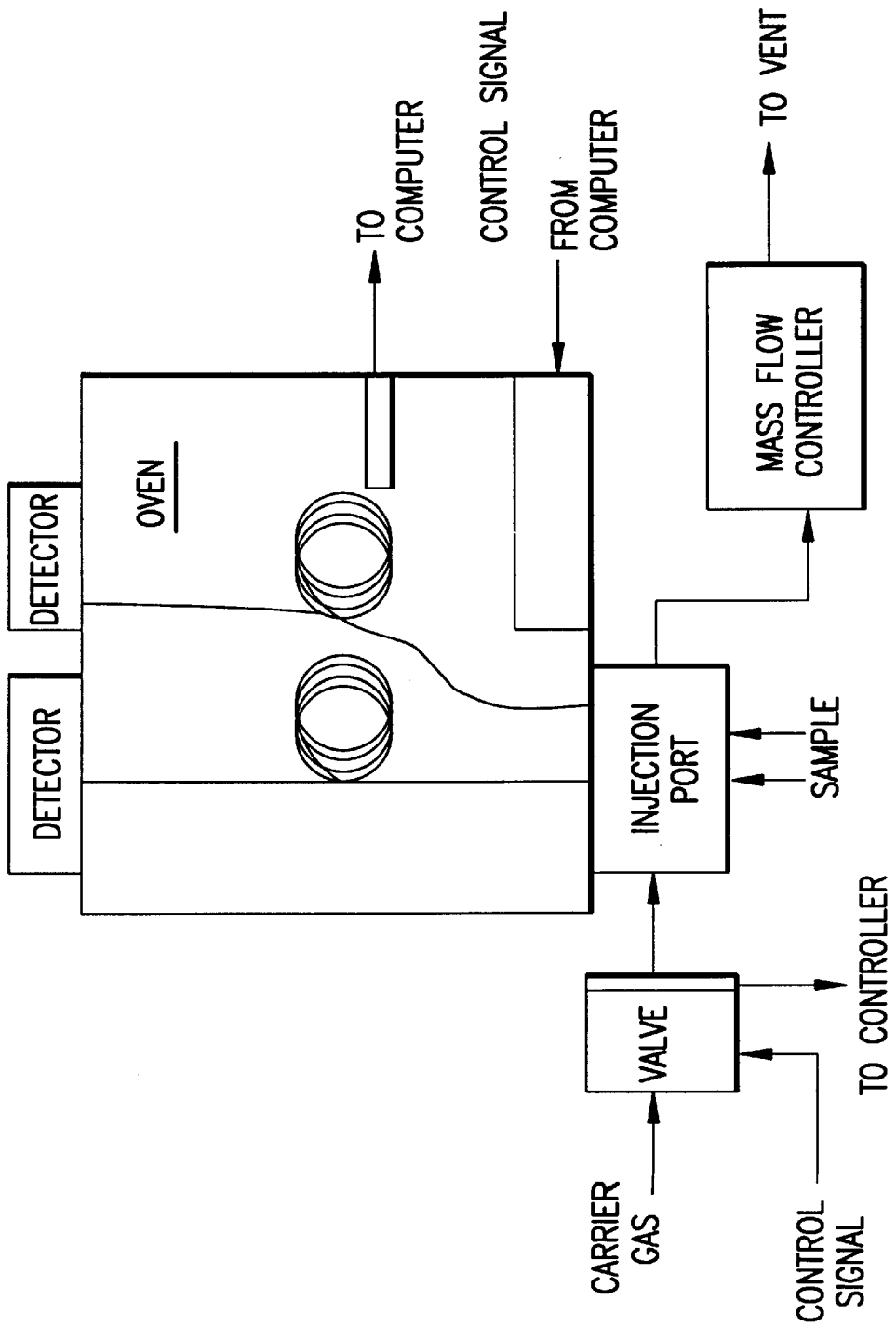
FIG. 4 illustrates a GC system having two columns operating in parallel.
Figure 5:
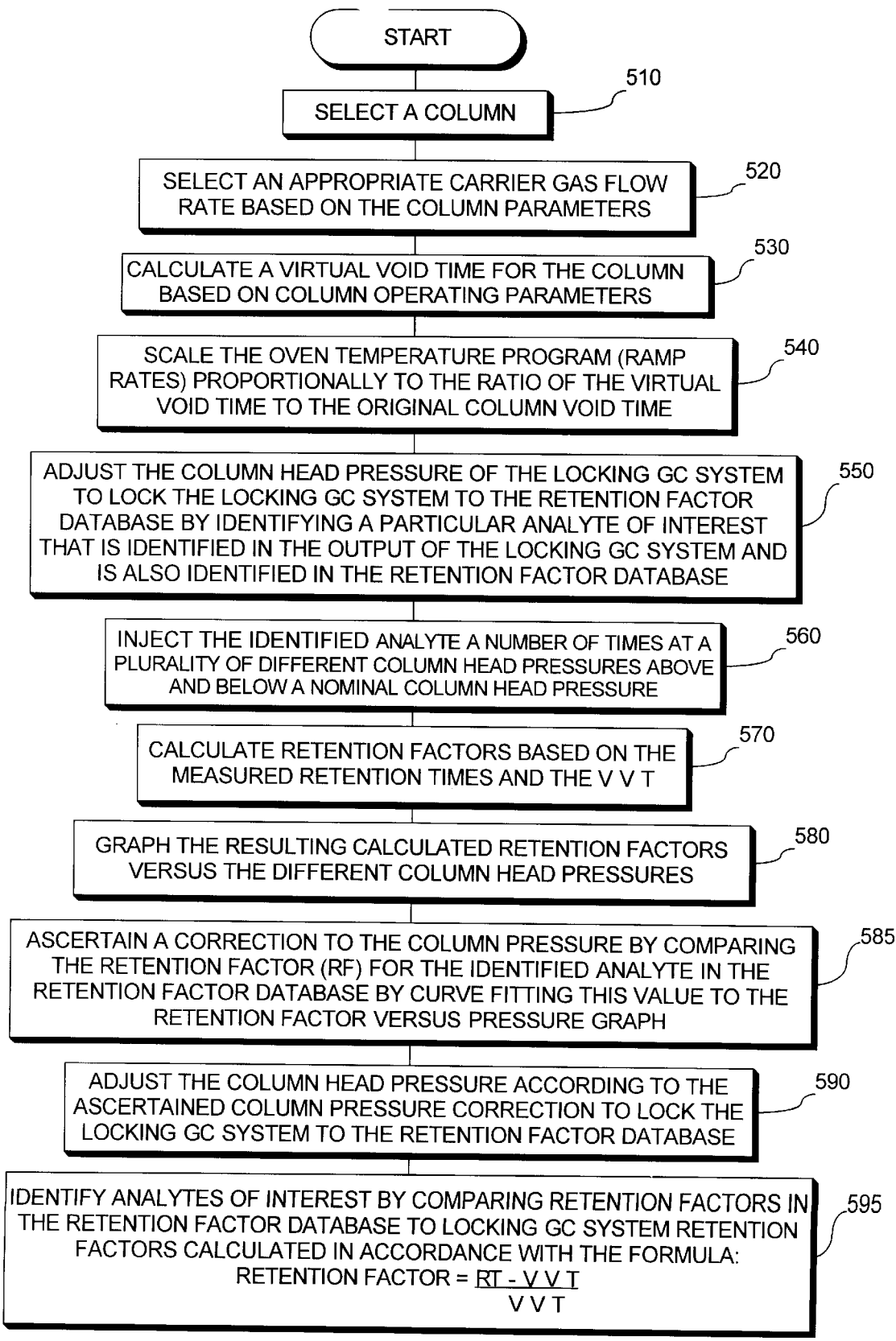
FIG. 5 is a flow chart illustrating the method steps for locking a locking GC system having a column with a virtual void time.

Additional discrimination may be obtained through the use of analyte selective detection as disclosed in copending patent application Ser. No. 08/846,977, filed on Apr. 30, 1997 by Matthew S. Klee et. al. now U.S. Pat. No. 5,827,946 entitled "Method For Sample Identification Using a Locked Retention Time Database" and hereby incorporated by reference, may be employed for further discrimination when identifying analytes of interest. FIG. 4 illustrates a typical GC system that may be employed for practicing the invention. While two columns and two detectors are illustrated, a single channel GC system only incorporating one column and one detector is typically employed. The use of two columns ensures that the temperature profile applied to each column is identical such that measurement taken from two different types of detectors may be compared. For example, since retention factors automatically compensate for variations in the inlet and outlet pressures between two GC systems, it is possible to match retention factors generated on a GC/AED and a GC/MS even though the column outlet pressures are much different: 1.5 psi above ambient pressure for the AED and vacuum for the MSD. The procedure also compensates for differences in GC column length resulting from variations in manufacturing or from column cutting required during routine maintenance.

In an alternative embodiment, the invention can be practiced without actual knowledge of column void time. A column is first selected according to the needs (such as speed, resolution and carrier gas type) of the chromatographer (step 510). An appropriate flow rate for the carrier gas is determined based on the column parameters (column type, length, inside diameter, stationary phase etc.) of the selected column (step 520). The virtual void time for the column is calculated based on the operating parameters (carrier gas, starting temperature and the flow rate etc.) (step 530). As previously discussed in reference to the preferred embodiment, the oven temperature program (ramp rates) employed for generating the retention factor database are scaled for the column and operating parameters employed with the new GC system (step 540). In particular, the temperature ramp rates and the hold up times are scaled proportionally to the ratio of the virtual void time to the original column void time. The column head pressure of the locking GC system is adjusted to lock the locking GC system to the retention factor database by identifying a particular analyte of interest that is identified in the output of the locking GC system and is also identified in the retention factor database (step 550). The identified analyte is injected a number of times at different column head pressures above and below a nominal column head pressure (step 560). The retention factors are calculated based on the measured retention times and the VVT (step 570). The resulting calculated retention factors are graphed versus the different column head pressures (step 580). A correction to the column pressure correction is ascertained by comparing the retention factor (RF) for the identified analyte in the retention factor database by curve fitting this value to the retention factor versus pressure graph (step 585). The column head pressure is adjusted according to the ascertained column pressure correction to lock the locking GC system to the retention factor database (step 590). Analytes of interest may now be identified by comparing retention factors in the retention factor database to locking GC system retention factors calculated in accordance with the formula:

$$\text{retention factor} = \frac{RT - VVT}{VVT} \quad \text{(step 595)}$$

While the invention has been described and illustrated with reference to specific embodiments in the area of calculating retention factors and temperature program ramp rates based on column void time, those skilled in the art will recognize that modification and variations may be made such that the invention, and in particular, temperature ramp rates may be calculated equally well through the use of a nominal void time that approaches the void time, and a virtual void that is calculated based on column and operating parameters.

What is claimed is:

1. A method for identifying analytes of interest eluting from a locking GC system by retention factor k, comprising the method steps of:

generating a retention factor database corresponding to a plurality of identified analytes independent of column dimensions and carrier gas type while dependent upon stationary phase type and ratio and a relative temperature program, the step of generating a retention factor database further comprising the method steps of:

adjusting the column head pressure of a reference GC system to ensure reproducibility of retention times by locking the column void time to a specific value, measuring the void time (VT) of the column, injecting a series of known analytes (standards) into the reference GC system operating at a specified temperature program denoted in multiples of void time, and measuring the retention times of the known analytes, calculating the retention factor (k) for each of the known analytes in accordance with the following formula:

$$k = \frac{(RT - VT)}{VT}$$

where VT is the void time of the column having a specified stationary phase coating installed on the reference GC system operating in accordance to the specified temperature program (where time is expressed in units of column void time), injecting an unknown sample to be identified into a column on the locking GC system, the column having the same stationary phase type and ratio of that employed on the reference GC system and a temperature program, measuring the retention times of analytes as they elute from the column, calculating the retention factor k, in accordance with the following formula:

$$k = \frac{(RT - VT)}{VT}$$

identifying analytes of interest by their retention factor k stored in the retention factor database.

2. The method for identifying analytes of interest by retention factor, as claimed in claim 1, further comprising the step of scaling a locking GC system temperature program in units of void time to match the specified temperature program in units of void time of the reference GC system employed for generating the database.

3. The method for identifying analytes of interest by retention factor, as claimed in claim 2, further comprising the step of:

adjusting the column head pressure on the locking GC system to maintain a constant column void time, thereby locking all retention times of the analytes of interest.

4. The method for identifying analytes of interest by retention factor, as claimed in claim 2, further comprising the step of:

identifying one analyte of interest and its retention time, adjusting the column head pressure on the locking GC system to maintain a constant retention time for the identified analyte of interest, thereby locking the retention times of all the other analytes of interest.

5. The method for identifying analytes of interest by retention factor, as claimed in claim 2, further comprising the step of:

installing a new column in the locking GC system having the same stationary phase and phase ratio as on the column in the reference GC system used to generate the retention factor database, measuring the void time of the new column, operating the locking GC system in accordance with the locking GC system temperature program that is scaled by units of void time to the specified temperature program employed for generating the database, calculating retention factors (k) for analytes of interest in accordance with the following formula:

$$k = \frac{(RT - VT)}{VT}$$

where VT is the void time of the column having a specified stationary phase and phase coating installed in the locking GC system operating in accordance to a specified temperature program (where time is expressed in units of column void time), and identifying analytes of interest by matching the calculated retention factor with the retention factor database, wherein the retention factor database is accessible by a variety of different locking GC systems employing different column dimensions, carrier gas types under possibly different inlet and outlet pressures for the identification of analytes of interest based on the retention factor (k) alone.

6. The method for identifying analytes of interest by retention factor, as claimed in claim 5, further comprising the step of:

accessing the retention factor database over the Internet, the database containing retention factors corresponding to a chromatographic method having broad application, scaling the retention factors for use in identifying analytes of interest separated on a plurality of locking GC systems operating under locked conditions, wherein individual requirements for speed, resolution, carrier gas type, or column capacity are provided for.

7. A method for identifying analytes of interest eluting from a locking GC system operated in accordance with an oven temperature program, by retention factor and reference to a retention factor database, comprising the method steps of:

selecting a column according to the needs of the chromatographer, determining a first column head pressure for the locking GC system based on one or more column parameters of the selected column and requirements for speed and efficiency, calculating a virtual void time (VVT) for the selected column based on the locking GC system operating parameters and the column parameters of the selected column, determining a new oven temperature program by scaling the oven temperature program ramp rates employed for generating the retention factor database for the column and operating parameters employed with the locking GC system, adjusting the first column head pressure of the locking GC system to a second column head pressure to lock the locking GC system to the retention factor database by identifying a particular analyte of interest that is identified in the output of the locking GC system and is also identified in the retention factor database, injecting the identified analyte a number of times at different column head pressures above and below the second column head pressure, detecting the retention time at which analytes of interest elute from the column, calculating retention factors based on the measured retention times and the VVT, graphing the resulting calculated retention factors versus the different column head pressures, measuring a current column head pressure being applied to the column, measuring the column head pressure currently being applied to the column, ascertaining a correction to the current column head pressure by comparing the retention factor (RF) for the identified analyte in the retention factor database by curve fitting this value to the retention factor versus pressure graph, adjusting the current column head pressure according to the ascertained column head pressure correction to lock the locking GC system to the retention factor database, and identifying analytes of interest by comparing retention factors in the retention factor database to locking GC system retention factors calculated in accordance with the formula:

$$\text{retention factor} = \frac{RT - VVT}{VVT}.$$

* * * * *